(12) United States Patent
Baldwin et al.

(10) Patent No.: US 8,252,519 B2
(45) Date of Patent: *Aug. 28, 2012

(54) PROCESS FOR CONTINUOUS PRODUCTION OF BACTERIOPHAGE

(75) Inventors: Douglas Baldwin, College Station, TX (US); Neil S. Summer, College Station, TX (US)

(73) Assignee: Phage Biocontrol Research, LLC, College Station, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/175,511

(22) Filed: Jul. 1, 2011

(65) Prior Publication Data

US 2012/0040329 A1   Feb. 16, 2012

Related U.S. Application Data

(60) Provisional application No. 61/373,215, filed on Aug. 12, 2010.

(51) Int. Cl.
*C12Q 3/00* (2006.01)
*C12N 7/00* (2006.01)
(52) U.S. Cl. .......................................... 435/3; 435/235.1
(58) Field of Classification Search .................... None
See application file for complete search history.

(56) References Cited

U.S. PATENT DOCUMENTS

| | | | |
|---|---|---|---|
| 4,442,895 A | 4/1984 | Lagus et al. | |
| 4,778,653 A | 10/1988 | Kamimuta et al. | |
| 5,160,433 A | 11/1992 | Nielsen | |
| 6,699,701 B1 | 3/2004 | Sulaknalidze et al. | |
| 6,926,833 B2 | 8/2005 | van Reis | |
| 2009/0180992 A1 | 7/2009 | Summer et al. | |
| 2010/0243563 A1 | 9/2010 | Summer et al. | |
| 2011/0281329 A1 | 11/2011 | Lenherr et al. | |

FOREIGN PATENT DOCUMENTS

| | | | |
|---|---|---|---|
| WO | WO 02/40642 | | 5/2002 |
| WO | WO 2010/068366 | * | 6/2010 |

OTHER PUBLICATIONS

Sakaguchi, et al (Control of Microbiofouling Using Bacteriophage 2. Detection of Phages and Fundamental Study of Their Lytic Effect on Fouling Bacteria (Abstract Only), De, 1989.

Lee, et al (Molecular analysis of a mixed-species biofilm on carbon steel. Abstracts of the General Meeting of the Americam Society for Microbiology. 2003; vol. 103:Q-156).

Zacheus et al, Soft Deposits, The Key Site for Microbial Groth in Drinking Water Distribution Networks; Wat. Res. Vi ol. 35, No. 7, pp. 1757-1765, 2001.

* cited by examiner

*Primary Examiner* — Shanon A Foley
(74) *Attorney, Agent, or Firm* — Douglas Baldwin

(57) ABSTRACT

As bacteriophage use in industrial application grows there is a need for commercial quantities of identified bacteriophage. This invention discloses a continuous flow bacteriophage proliferation process that can provide commercial quantities of desired bacteriophage in concentrations suitable for industrial use. Host bacteria and virulent bacteriophage are fed into a reactor vessel where the phage attach to, infect and lyse the host bacteria providing multiple replications of it and coincidentally concentrating the phage.

15 Claims, 4 Drawing Sheets

PROCESS FOR CONTINUOUS PRODUCTION OF BACTERIOPHAGE

RELATION TO OTHER APPLICATIONS

The present application claims benefit under 35 U.S.C. §119(e) of U.S. Provisional Patent Application No. 61/373,215, filed Aug. 12, 2010, entitled "Process for Continuous Production of Bacteriophage" the disclosure of which is hereby incorporated by reference in its entirety for all purposes.

FIELD OF THE INVENTION

This invention relates to the production and concentration of bacterial virus or bacteriophage in a device named herein as a "proliferator". More specifically it relates to a method of continuous production of bacteriophage by combining host bacteria with virulent bacteriophage or similar virus in a continuous flow reactor vessel under conditions of temperature, solution composition and residence time, designed to replicate the virulent virus or bacteriophage, thereby increasing both the number and concentration of bacteriophage in the circulating solution.

BACKGROUND

Interest in the use of bacteriophage viruses has increased significantly in the last several years, but commercialization usage is still in the early stages. Resistance to antibiotics has driven the interest in bacteriophage medical therapy and the safety and efficacy of bacteriophage for food stuff sterilization and industrial applications has driven interest in these areas. Industrial applications such as remediation of bio-fouling in water systems, microbial induced corrosion (MIC) in water systems and especially in the oil and gas and pipeline industries have generated a need for adequate processes for large scale production of bacteriophage. See published applications US 2009/0180992, published Jul. 16, 2009 and US 2010/9243563 published Sep. 30, 2010.

For industrial applications the need is for relatively large amounts of phage, beyond the scope of laboratory production. Moreover, the concentration/proliferation of bacteriophage which exist in aqueous solutions in fairly low absolute concentrations requires processing a large amount of water.

This invention is an efficient continuous flow bacteriophage concentrator/proliferator which will concentrate bait bacteriophage from fluid in separate receptacles, while filter sterilizing the fluid into the appropriate media for a three way combination to proliferate the desired phages of viruses.

SUMMARY OF INVENTION

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

This invention is a method or process for the production of virulent bacteriophage and other phage-like viruses in a continuous flow reactor or proliferator. More specifically, in one embodiment, it is a method of continuous production bacteriophage comprising contacting target bacteria with virulent bacteriophage in a continuous flow reactor vessel having an inlet and outlet under conditions of temperature, solution composition and residence time to replicate virulent bacteriophage, thereby increasing both the number of bacteriophage and the concentration of phage in the circulating solution. In another embodiment bacteriophage and host or bait bacteria are obtained from source water containing the same by filtration through appropriate sized filters to obtain a solution of host bacteria and a solution of matching phage. In another embodiment it is the process described above but with continuous analysis of critical streams in the process to allow control of process flow rates.

DESCRIPTION OF DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION

This invention is a method of continuous bacteriophage production comprising a "proliferator" in which target "bait" bacteria and matching virulent bacteriophage are combined in a continuous flow reactor vessel under conditions of temperature, solution composition and residence time to replicate virulent bacteriophage, thereby increasing both the number of bacteriophage and its concentration in solution. Phage concentration of the reactor outflow can be adjusted by the relative flow and concentration of input bacteria solution and bacteriophage solution, residence time and optionally, recycle of the output stream. The invention also provides for the control of flows in the reaction in response to real time analysis of component streams.

As used herein the following definitions apply: A phage cocktail includes multiple, receptor independent phages for each target bacterial host. This is different from a phage panel, which is a collection of phages chosen to cover as wide a host range as possible. Since some SRB phages are known to be polyvalent—effective against more than one strain of SRB (or other bacteria), there may not need be a separate cocktail for every strain of target bacteria. This panel of cocktails is designated herein as phage "multi-panel".

As used herein, the terms bacteriophage and virus are used interchangeably. This is because biologists have not consistently named all phage-like viruses as phage. For example, archaea, are preyed upon by archae virus, Algae, by algal virus and fungi by mycovirus. All such virus and bacteriophage that replicate in the same way as bacteriophage are candidates for the process of this invention. Bacteriophage also include engineered bacteriophage, that even thought modified from the "wild" phage (as found in natural state) will replicate in the same or similar way as "wild" phage.

Phage Concentration and Proliferation

In order to produce sufficient amount of bacteriophage (phage) to treat large volume of water, phage numbers may be greatly increased and concentrated either on site of use or at a central location. Propagation of virulent phages is achieved by attaching itself into its matching host bacteria, infection the host, replicating itself and rupturing the bacteria.

Figure 1:
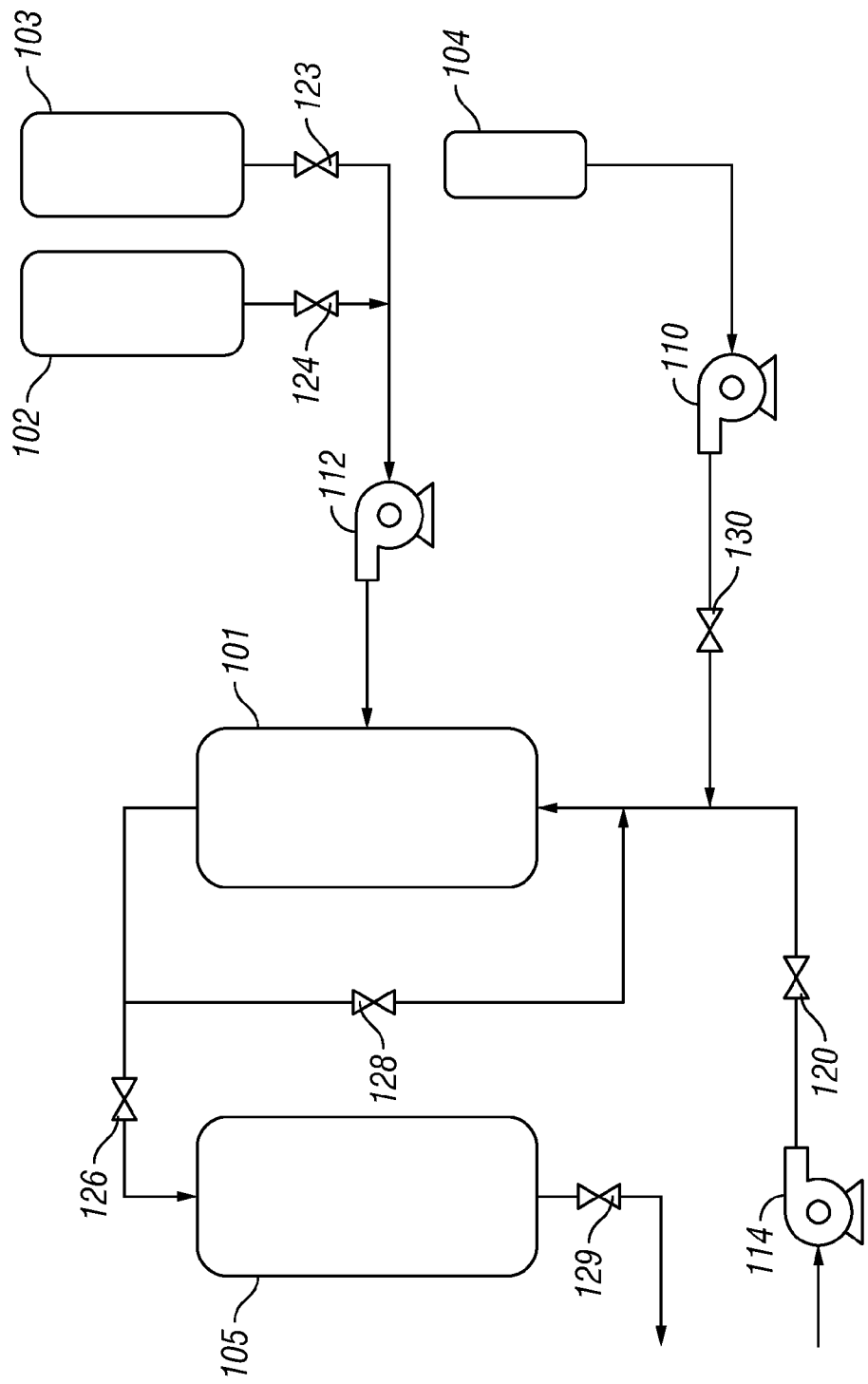
FIG. 1 is a schematic representation of an embodiment of the invention.

An embodiment of this invention is a process for bacteriophage concentration and proliferation as illustrated in FIG. 1. When bacteriophage to be concentrated are anaerobic as are sulfate reducing bacteria (SRB) it is preferred, and sometimes necessary for the entire system for proliferation/concentration to be blanketed with a non-oxygen gas—nitrogen preferred, since the SRB will not survive if there is significant oxygen in the system. This precaution may not be required for phage of aerobic bacteria (such as Nocardonia and Gardonia) but may be used to reduce air born contamination of the system.

There are many factors that influence the rate and efficiency of attachment of phage to host bacteria and the lyse of the problematic bacteria, including, but not limited to, temperature, pressure, medium in which they reside and concentration. Concentration of both phage and bacteria are often critical to achieve meaningful replication since interaction between phage and bacteria is largely governed by the concentrations of both the phage and the host bacteria. Mathematical models allow a theoretically calculation of the dynamics of the host and phage population change in a given system. Phage start the life cycle by adsorbing to the hose cell, and virulent phage adsorption to the host cell generally results in the destruction of the host cell and release of progeny phage. Unless the concentration is sufficiently high little replication will occur. Therefore, it is critical in the method of the invention that the concentration of bacteria and phage be sufficient for maximum infection and replication. This criticality of concentration is described in the following:

"The rate at which phages adsorb to their host is determined by second-order kinetics, as described by the relationship $-dp/dt=kPB$, where k is the phage adsorption rate constant in ml/min, P is the phage concentration, and B is the bacterial concentration. Although this process can be expressed in terms of second-order kinetics, under most conditions the behavior is pseudo-first order: during the adsorption process free phage are eliminated from the system by adsorption to a host bacterium, but the bacterium remains free in the system to adsorb additional phage. This relationship can also be expressed explicitly (here in terms of the rate constant k) as $$k = \frac{2.3 \times \log(P_0/P_t)}{B \times t}$$

where $P_0$ is the initial concentration of free phage and $P_t$ is the concentration of free phage at time t. One conclusion which can be drawn from this expression is that the concentration of susceptible bacteria, B, and the adsorption rate constant, k, will strongly influence the rate at which free phage are able to locate and adsorb to their hosts. A second conclusion is that given constant parameters, the amount of phage adsorbed by bacteria in time period t is a constant proportion of the initial phage population. Thus, if 50% of the free phage in a given system are adsorbed during time t, the absolute number of phage adsorbed would be 50 if $P_0=100$ PFU, and 50,000 if $P_0$ were 100,000 PFU." (Practical and theoretical considerations for the use of bacteriophages in the food systems, Jason J Gill, in *Bacteriophages in the control of food and waterborne pathogens*, Parviz M Sabour and Mansel W Griffiths ed., June 2010, American Society for Microbiology Press, Washing D.C.)

Theoretical calculations based on the mathematical models, while are not the only factors covering phage replication, serve as guidelines for determining the amount of phage and the time required to replicate phage under ideal conditions. For example, Table 1 shows the time (in minutes) required to adsorb a given percentage of phage (for example, 50%, 90%, and 99%) as a function of the target cell concentration (in CFU/ml), assuming $k=5 e^{-8}$ ml/min (a fast binding rate). Note this proportion is independent of the actual number of phage, so 50% of 100 PFU/ml means 50 PFU/ml bound, and 50% of 1,000,000 PFU/ml means 500,000 PFU/ml bound.

TABLE 1

The time (min) required to adsorb a given percentage of phage (in minutes) as a function of the target cell concentration (CFU/ml), assuming $k = 5e^{-8}$ ml/min (a fast binding rate).

| Bacteria concentration | Time, Minutes - % Phage absorbed | | |
|---|---|---|---|
| CFU/ml | 50% | 90% | 99% |
| $1 \times 10^5$ | 138.6 | 460.5 | 921.0 |
| $5 \times 10^5$ | 27.7 | 92.1 | 184.2 |
| $1 \times 10^6$ | 13.9 | 46.1 | 92.1 |
| $5 \times 10^6$ | 2.8 | 9.2 | 8.2 |
| $1 \times 10^7$ | 1.4 | 4.6 | 1.8 |
| $5 \times 10^7$ | 0.3 | 0.9 | 0.9 |
| $1 \times 10^8$ | 0.0 | 0.5 | 0.2 |
| $5 \times 10^8$ | 0.0 | 0.1 | 0.2 |

Based on the above theoretical calculations, it is necessary to have some idea about the amount of bacteria that need to be replicated for effective and timely phage attachment, infection and lyse of target bacteria, To kill as many target bacteria as possible, target cell concentration is less relevant as long as enough phage can be introduced into the system to adsorb greater than 90% the cells in a timely manner. On the other hand, in a situation where timely amplification of phage (net gain of progeny phage after lysis) is desired, relative high concentrations of bacteria (greater than $10^6$-$10^7$ CFU/ml) are required. Thus, for practical application virulent phage and target bacteria concentrations will need to be above $10^6$ particles/ml to achieve meaningful replication of phage and destruction of bacteria, assuming a medium to high rate constant k. The bacteriophages that may be concentrated and/or produced by this invention span the range of virulent bacteriophages, including engineered phages. The invention is most useful where large amounts of phage are required, as for example, in treatment of industrial bio-fouling in water systems, pipelines, oil and gas reservoirs and equipment and the like. In these applications, it will often be requires to prepare multiple bacteriophage, as for phage panels, phage cocktails and phage multi-panels.

Referring to FIG. 1, vessel 101 is a concentrator/proliferator. Water containing target bacteria is pumped into vessel 101 through valve 120 (by pump 114) where it is mixed in continuous flow with a bacteriophage panel or multi-panel virulent for the target bacteria strains, shown as being pumped, 110, through valve 130 from vessel 104 to be mixed with the incoming bacteria-containing water in vessel 101.

Some forms of SRB bacteria will be substantially destroyed by its virulent phage in less than 20 minutes. The concentrator vessel is sized to provide a flow rate of concentrated bacteriophage solution sufficient to treat the desired volume of water for immediate use or storage. A 4 ft diameter vessel will have a volume of 12.6 ft$^3$/ft of height. A 6 ft diameter vessel will have 28.3 ft$^3$/ft. Thus, a 4 ft diameter vessel, 8 ft tall will contain 100.8 ft$^3$ and a 6 ft diameter vessel, 8 ft tall will contain 226.4 ft$^3$.

A flow rate of 9.3 gpm in the 4 ft. diameter reactor and 37.7 gpm in the 6 ft. diameter reactor will provide 20 minute residence time (equivalent to the time needed for substantially complete destruction of some strains of SRB bacteria).

Concentration of bacteriophage in the solution leaving vessel 101 depends, to an extent, upon the concentration of target bacteria in the incoming water. When matching bacteria is present some phages may be replicated by a factor of about 20:1. Therefore, for example, when the incoming water contains 2×10$^6$ pfu/ml the outgoing stream will contain 4×10$^7$ pfu/ml. If the replication is 100:1 then the out stream will have a phage concentration of 1×10$^8$ pfu/ml—a two orders of magnitude increase. If replication is only 10:1 the outlet stream will increase in concentration by one order of magnitude to 1×10$^7$. The phage will continue replicating so long as it can effectively contact target bacteria in the water. Thus, the replication will continue when the outgoing concentrated phage solution is mixed with bacteria-containing water, as for example in storage vessel 105. However when the concentration of bacteria or phage falls much below 1×10$^6$ particles/ml the infection and replication slows to essentially non-activity.

Initially the concentrator/proliferator is fed with a solution of bacteriophage multi-panel (mixture of virulent phages) that have been separately generated—shown in vessel 104 and passed to the concentrator/proliferator through valve 130. Once the concentrator is functioning phage(s) may be supplied by recycle of a portion of the output stream through valve 128. The amount of recycle will preferably be sufficient to provide a phage to target bacteria ratio of from 1 to 0.001. In general, the recycle will contain about 20 times the concentration of phage as the concentration of target bacteria in the source water since some SRB phages will replicate in target bacteria about 20:1. Some of the concentrated phage solution may be stored, as in one of the temporary storage tanks, 105, for future use.

In FIG. 1 vessel 101 contains phages virulent for the target bacteria used to start the process. It may be replenished by recycle of the concentrated outflow of the phage concentrator 101 or from an external source. Thus, in operation, the phage concentrator will take in target bacteria containing water through valve 120. In either case, the phages will continue replicating if there are target bacteria present, substantially destroying the target bacteria. Reactor vessel 101 may contain packing such as ceramic balls, spheres and other shapes or inert fibers, mesh and the like to enhance mixing and bacteria/phage contact/

Vessels 102 and 103 are used for culturing target bacteria which may optionally be added to the concentrator/proliferator 101 through valves 123 or 124 by pump 112 to increase the concentration of incoming bacteria and hence the amount of phages produced. Such supplemental bacteria may also be varied to generate a desired mix of phage in the output stream. Culturing of bacteria may be conducted on-site or at a centralized location.

Alternatively target bacteria may be concentrated from source water in a tangential flow filter system. Such a system is illustrated in FIG. 2.

Figure 2:
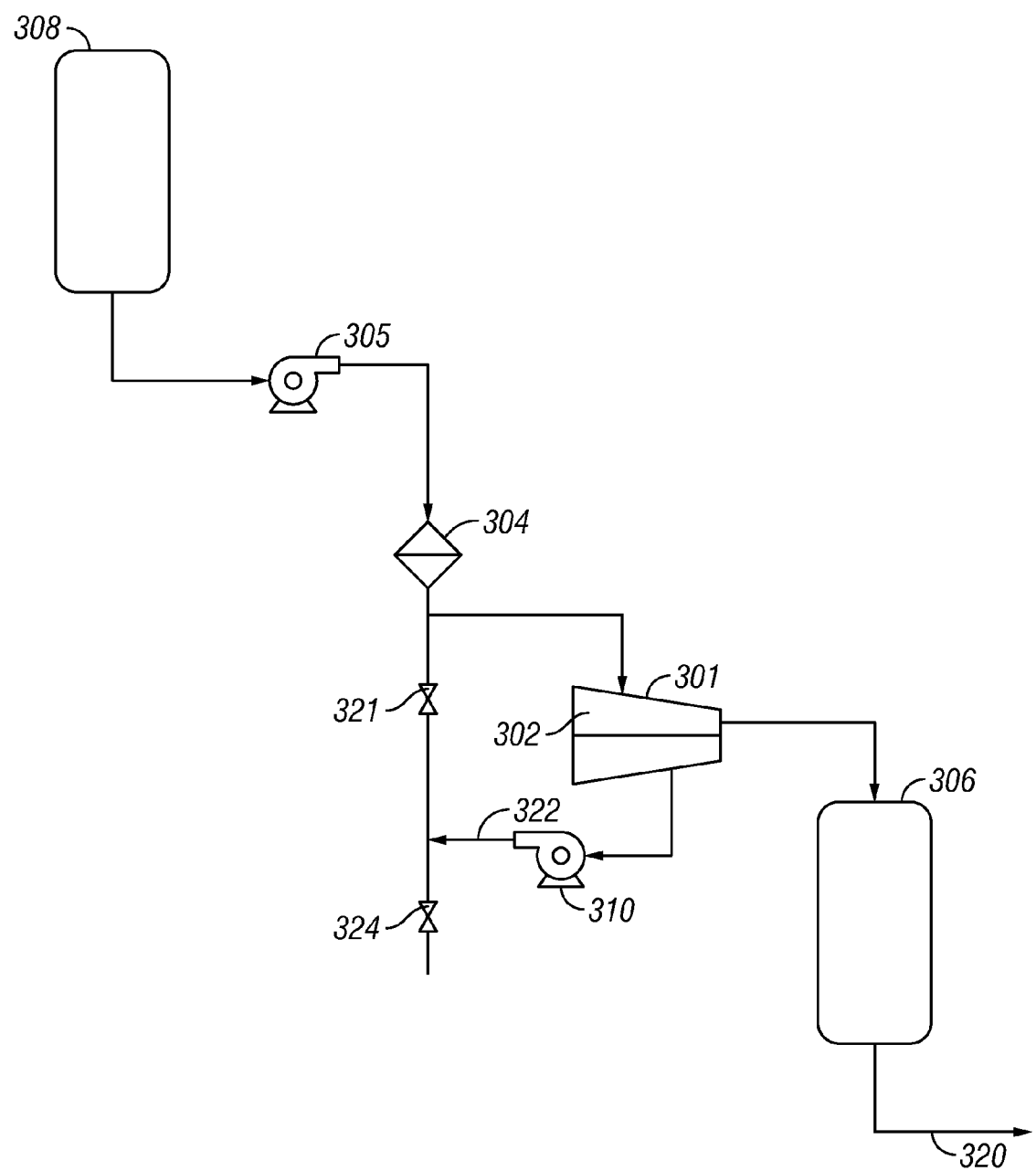
FIG. 2 is schematic representation of an aspect of the invention.

Referring to FIG. 2 water is pumped from storage 308 by pump 305 to filter 304—a coarse filter to remove larger particles and trash. From filter 304 the water passes by conduit 321 to tangential flow filter 301, having a filter screen, 302, of about 0.2 micron. The screen is sized to hold back SRB bacteria and let smaller particle pass. The filter water may be recycled to the filter by pump 310 (conduit 322). The filtrate passes to tank 306 where it may be directed as needed through conduit 320.

The illustration in FIG. 2 shows the water source in vessel 308. The water source may be any suitable source that contains target bacteria. In one embodiment the source will be the "produced" water from oil or gas wells. In general, "produced" water will contain salts (e.g. NaCl) and the problematic target bacteria will be halophilic. Thus, source bacteria that cannot survive or thrive in salt water will not be a problem in the well or reservoir. It will be desirable to isolate target halophilic bacterial from the well bore and formation. Such bacteria can also be cultured as described above by using a brine culture solution.

Figure 3:
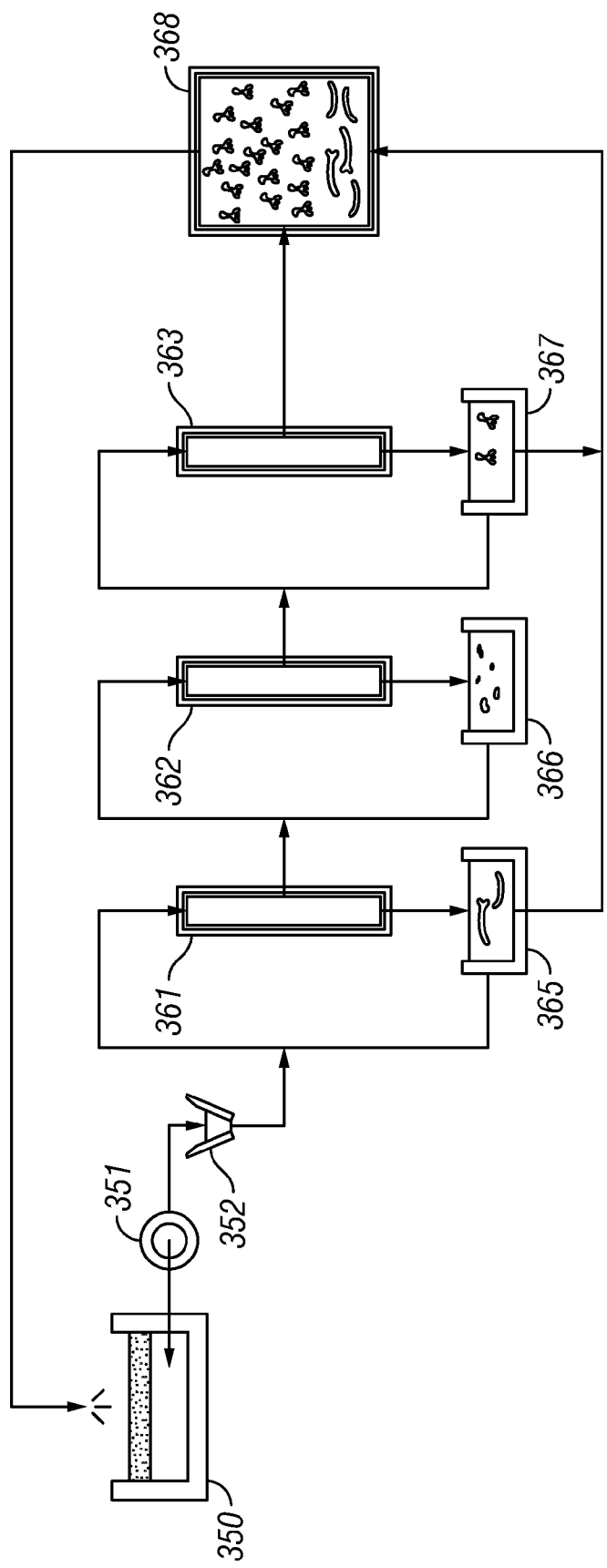
FIG. 3 is schematic representation of an embodiment of the invention.

FIG. 3 illustrates yet another more detailed three stage embodiment of the process of the invention applied to filamentous bacteria—it is equally applicable to other kinds of bacteria such as SRB. The first section of the embodiment comprises of an intake filter (352) of ⅛"mesh, a 1-2" trash pump, a sonicator (351) of "cleaning" vs. "cell disruption" frequency, a coarse filter (352), followed by series of tangential, or cross flow filters to provide size separated streams. Referring to FIG. 3 phage and bacteria are pumped from a source container, 350, through an Ultrasound Flow Disrupturer (sonicator) (351, into the first stage filter 361 (Stage 1) to tank 365. Return lines serve to further concentrate the size samples. Flow passes through the initial conical particulate filter of 150 micron mesh size (Course Filter) so that flow containing particles of less than 150 micron will enter a 20 micron filter (Stage 1). Outflow from the stage filters will be contained in tanks 365, 366 or 367 as shown. The permeate will contain particles smaller than 20 microns. The stream will contain the particle size fraction 150-20 micron. In one embodiment, this size fraction will correspond to target bait filamentous bacteria. The 20-0.2 micron size will contain the bulk of the remaining bacterial species present in the intake fluid. In another embodiment this size fraction may contain target bacteria, or may be a waste stream. The retentate stream can be routed back for multiple passes. The permeate stream of particles smaller than 0.2 micron (from Stage 2 Filter, 361) will pass through a 100 kilodarcy (KD) cross flow filter (Stage 3, 363). The permeate will comprise of near sterilized fluid, the retentate will comprise of viral particles, including the required virulent phage and is passed to storage 368. The near sterilized filtered fluid the "liquor" will constitute an ideal growth media. The appropriate size fraction corresponding to the desired bait bacteria, combined with the viral fraction in the "liquor" all at the most appropriate relative percentages will constitute the feed stream for a proliferator as in FIG. 1.

Figure 4:
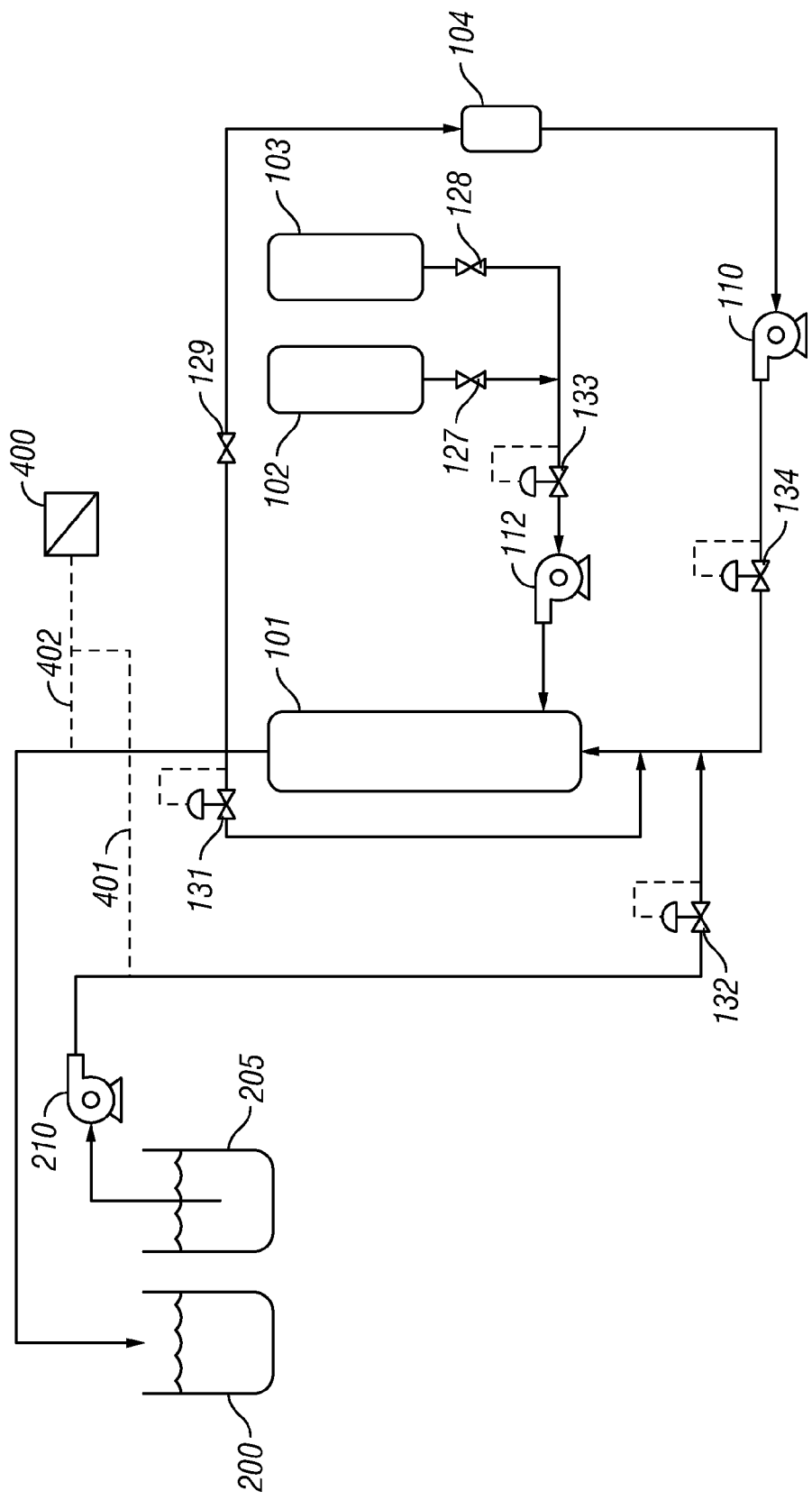
FIG. 4 is a schematic representation of an embodiment of the invention.

In another embodiment the invention comprises the concentrator/proliferator, described above, with a real time analyzer/controller. The operation of the concentrator/proliferator with means for real time phage counting and control is illustrated in FIG. 4.

Process Monitoring and Control by Real Time Analysis

Vessel 101 (FIG. 4) is a bacteriophage concentrator/proliferator. Water containing target bacteria is pumped from source 200 or 205 by pump 210 into vessel 101 through control valve 132 where it is mixed with bacteriophage virulent for the target bacteria, shown as being pumped with pump 110 through control valve 134.

Initially the concentrator/proliferator will be fed with bacteriophage that has been separately generated—vessel 104—and passed to the concentrator/proliferator through control valve 134. Once the concentrator/proliferator is functioning the bacteriophage phage is supplied by recycle of outgoing stream of phage concentrate through control valve 131 and phage from vessel 104 can be stopped.

Unit 400 in FIG. 4 represents a real time analyzer/controller capable of determining both phage type and count and with control means (such as a specially programmed computer connected to control means) that is connected to control valves, such as 131 132, 133 and 134. The analytical means of unit 400 is fed sample streams (or spot samples) as illustrated by dotted lines 401 and 402. The analyzer will determine the type and/or count of bacteria and of bacteriophage and pass the results to the control means of unit 400. The control means is programmed to adjust the flow through control valves 131, 132, 133 and 134 to achieve predetermined ratios and concentrations in the flow streams. Real time measurement makes it possible to adjust the flow rates of source water and bacteriophage solution as conditions change. For example if the outflow stream is too low in phage concentration, additional bacteria may be provided to increase the replicated phage thus increasing the concentration. Real time measurement is also useful in determining when sufficient bacteriophage has been added to the source water to effect adequate destruction of target bacteria. The analyzer means may also be configured to allow read-out of concentration of bacteria and bacteriophage in the sample streams.

The control means of unit 400 and of this invention, can easily be designed by those skilled in the art and is commercially available for purchase.

The real-time analytical means for bacteria and/or bacteriophage is not so readily available at this time. Wet chemical analytical means are available but take considerable time and, while useful, will not be ideal. For example, test kits are readily available to measure SRB bacteria count such as Sani-Check SRB Test System; a kit that contains tubes of culture media specifically formulated to promote the growth of anaerobic sulfate reducing bacteria and available from Biosan Laboratories, Inc., 1950 Tobsal Court, Warren, Mich. 48091-1351. Analysis of bacteria count, but not phage count, can be made by serial dilution to achieve a sufficient diluted concentration that the bacteria count can be determined with an adequate microscope.

Single Particle Mass Spectrometry is the only current technology that can enumerate bacteria in real-time. Single Particle Mass Spectrometry (SPAMS) was on outgrowth of an analyzer developed (BioAerosol Mass Spectrometer—BAMS) for military and civilian biodefense applications and was, in fact, first fielded in response to the U.S. Postal Service anthrax attacks of late 2001. The SPAMS technology is described in WO 2010/068366 published Jun. 17, 2010, the disclosure of which is incorporated herein by reference. SPAMS remains the only real-time technique that can detect, identify and quantify bacteria in real-time and has the added advantage of requiring no reagents and little or no sample preparation, consuming only electricity and sampling particles directly from the air. The SPAMS operating principles are conceptually very simple. Particles, whether biological or not, are suspended in a carrier gas if they are not in such a gas already. The SPAMS system is maintained at vacuum and particles are driven in by product pressure. The particles are focused aerodynamically into a beam which is collimated by skimmers that separate the different stages of successively higher vacuum. The particles arrive at a tracking stage as a coherent beam of particles flying through high vacuum towards the center of the source region of a dual-polarity time-of-flight mass spectrometer. The particles are tracked by continuous wave laser(s) where their position and velocity are determined. This information is used to predict their precise time of arrival at the center of the source region and the velocity is used to determine their size. Upon their arrival at the source of the mass spectrometers, each particle is individually desorbed and ionized by a pulsed laser and the positive and negative ions are detected by their respective mass spectrometer. The mass spectra are analyzed in real-time by a two stage pattern recognition algorithm and the particles are identified accordingly. In this manner, biological organisms are identified to at least the genus and often the species level. Furthermore, because this process can be repeated at up to one kilohertz, the organisms can be detected and quantified even in a background of particles of thousands of times their own concentration.

SPAMS returns a fairly precise determination of the biological organisms being observed (genus to species level) at the low incremental cost of adding data to a digital library. The training process is highly automated as well, allowing non-pathogenic agents to be grown, analyzed and added to the library in hours or days. There is no other technology presently available that can detect biological organisms in real-time, identify them to the genus level, and return an answer in real-time.

The analysis of SPAMS data is a fairly important aspect of the system. Because SPAMS is a laser desorption/ionization technique, it tends to fragment the microorganisms into their small molecules with major metabolites being present at greater intensity than minor metabolites. The first stage of the analysis is the simple pattern recognition of the array of metabolites from the test mass spectra versus a library of previously collected mass spectra. Any mass spectra that are sufficiently similar are subjected to a rules tree where the presence and absence of different metabolites are used to confirm the identity of the microorganism. In this manner, SPAMS can discern, for example, *B. atrophaeus* spores from *B. thuringiensis* spores and can discern any form of *Bacillus* spore from any vegetative bacterial cell. Testing performed by independent referees for the Defense Advanced Research Projects Agency (DARPA) demonstrated the ability of SPAMS to discern one species of *Bacillus* spore from two others and one species of *Erwinia* vegetative cell from three others.

SPAMS systems are also extremely field rugged as has been proven generation after generation. The original BAMS 1.0 systems were deployed to the top of Mt. Wilson, to the Kashidoo Climactic Observatory and aboard the NOAA Ship Ronald H. Brown. The BAMS 1.5 system was operated during military training exercises at the National Training Center at Ft. Irwin for weeks in close proximity to military vehicles and ordinance. The BAMS 2.0 was operated successfully within 30 meters of a 10,000 lb. Spartan Stage I rocket motor "crack and burn" operation where the rocket motor was accidentally detonated when it was supposed to be deflagrated. Not only did the instrument survive but it continued to operate, confirming the absence of ammonium perchlorate in the plume for the Army.

Thus, in some embodiments of the invention is a phage production injection process as illustrated in FIG. 4 that utilizes a SPAMS derived analytical system and control to adjust the conditions and results of the process.

All vessels such as 101, 102, 103, and 104 are constructed of simple materials. They only need to be sufficiently strong to hold the solutions. Corrosion is not a particular problem although they should be able to contain "flowback" water which will have salt and chemical additives. It is desirable that they be able to be sterilized with bleach solution. Generally most plastic material used for tanks and vessels are suitable, including fiberglass, polypropylene, polyvinyl chloride and polyurethane. Stainless steel will also be suitable. Other commercially materials will be obvious to those skilled in the art. Since bacteria growth, and to some extent phage proliferation, is temperature sensitive there is provided in one embodiment means for heating either the inlet streams to the vessels or heating the contents of the vessels. The streams may be heated by heat exchange, electrical heaters or any other suitable means known in the art. The contents of the vessels may be heated with electrical or steam heaters or other suitable heating means.

These vessels are not especially heavy and the equipment is not extensive, therefore in one embodiment the proliferation/concentrator equipment—vessels 101, 102, 103, 104 and associated pumps, valves and piping—are mounted on a movable platform so that they can easily be transported from well site to well site. These can be mounted on skids (that can be lifted onto a truck bed), or on a trailer or truck bed.

Location of and commercial production of commercial scale phage virulent SRB as well as other phages can be accomplished by means described in prior art references such as published applications US 2009/0180992, published Jul. 16, 2009, US 2010/9243563 published Sep. 30, 2010, WO/2009/076642 and K. Kamimura and M. Araki: Isolation and Characterization of a Bacteriophage Lytic for *Desulfovrio salexigens*, a Salt-Requiring. Sulfate-Reducing Bacterium, Applied and Environmental Microbiology, March 1989, p. 645-648, Vol. 55, No. 3, the relevant disclosures of which are incorporated herein by reference. Other bacteria, including archaea may be similarly located, isolated and produced.

In this specification, the invention has been described with reference to specific embodiments. It will, however, be evident that various modifications and changes can be made thereto without departing from the broader spirit and scope of the invention as set forth in the appended claims. The specification is, accordingly, to be regarded in an illustrative rather than a restrictive sense. Therefore, the scope of the invention should be limited only by the appended claims.

The invention claimed is:

1. A method of continuous production bacteriophage comprising contacting target bacteria with bacteriophage in a continuous flow reactor vessel having an inlet or inlets and outlet or outlets, wherein a solution of bacteriophage virulent for target bacteria is continuously passed into the inlet or inlets of the reactor vessel and a solution containing replicated bacteriophage is continuously removed from the outlet or outlets of the vessel, in a manner that the solutions mix and flow together from inlet to the outlet while bacteriophage is replicating, under conditions of temperature, solution composition and residence time to lyse target bacteria thereby replicating bacteriophage virulent for target bacteria, and wherein the target bacteria and virulent phage are obtained by filtering with suitable tangential flow filters appropriate size solids from a source stream.

2. The method of claim 1 wherein a portion of the solution removed from the out or outlets of the continuous flow reactor vessel is recycled to the inlet to provide additional virulent bacteriophage for replication.

3. The method of claim 1 wherein combined input stream to the continuous flow reactor provide a target bacteria and virulent phage concentrations of at least $1\times10^6$ at the inlet.

4. The method of claim 3 wherein the residence time is sufficient to allow at least 50% lyse of target bacteria.

5. The method of claim 1 wherein the input and recycle streams are analyzed for bacteria and phage composition with real time analysis, which analysis is used to adjust flows to obtain desired reaction results.

6. The method of claim 1 wherein the target bacteria and virulent phage are obtained by filtering with suitable filtering means appropriate size solids from a source stream.

7. The method of claim 6 wherein the filtration means comprises tangential flow filters.

8. The method of claim 1 wherein the bacteria and virulent phage are the products of a three stage filtration system using tangential flow filters of appropriate size to isolate separate streams containing bacteria and virulent phage.

9. The method of claim 1 wherein the first stage of the three stages is sized to remove particles larger than bacteria, the second stage sized to hold back bacteria but let phage pass and the third stage size to capture phage.

10. A method of continuous production bacteriophage comprising contacting target bacteria with bacteriophage in a continuous flow reactor vessel having an inlet or inlets and outlet or outlets, wherein a solution of bacteriophage virulent for target bacteria is continuously passed into the inlet or inlets of the reactor vessel and a solution containing replicated bacteriophage is continuously removed from the outlet or outlets of the vessel, in a manner that the solutions mix and flow together from inlet to the outlet while bacteriophage is replicating, under conditions of temperature, solution composition and residence time to lyse target bacteria, thereby replicating bacteriophage virulent for target bacteria, and wherein the solutions removed from the outlet or outlets are analyzed for bacteria and phage composition with real time analysis, which analysis is used to adjust flows to obtain desired reaction results.

11. The method of claim 10 wherein the real time analysis is performed by a single particle aerosol mass spectrometer.

12. The method of claim 10 wherein a portion of the stream removed from the outlet or outlets is recycled to the inlet or inlets to provide additional virulent bacteriophage for replication and both the input and recycle streams are analyzed for bacteria and phage composition with real time analysis, which analysis is used to adjust flows to obtain desired reaction results.

13. The method of claim 10 wherein the solutions passed into the inlet or inlets and the solution removed from the outlet or outlets are analyzed for bacteria and phage composition with real time analysis, which analysis is used to adjust flows to obtain desired reaction results.

14. A method of continuous production bacteriophage comprising contacting target bacteria with bacteriophage in a continuous flow reactor vessel having an inlet or inlets and outlet or outlets, wherein a solution of bacteriophage virulent for target bacteria is continuously passed into the inlet or inlets of the reactor vessel and a solution containing replicated bacteriophage is continuously removed from the outlet or outlets of the vessel, in a manner that the solutions mix and flow together from inlet to the outlet while bacteriophage is replicating, under conditions of temperature, solution composition and residence time to lyse target bacteria, thereby replicating bacteriophage virulent for target bacteria, and wherein target bacteria are anaerobic and the solutions passed to the inlet or inlets, and removed from the outlet or outlets and the reactor is operated to exclude oxygen.

15. The method of claim 14 wherein reactor vessel is blanketed with a non-oxygen gas during operation.

* * * * *